(12) United States Patent
Karger et al.

(10) Patent No.: US 6,372,353 B2
(45) Date of Patent: *Apr. 16, 2002

(54) COATED SURFACE COMPRISING A POLYVINYL ALCOHOL (PVA) BASED COVALENTLY BONDED STABLE HYDROPHILIC COATING

(75) Inventors: Barry L. Karger, Newton; Wolfgang Goetzinger, Boston, both of MA (US)

(73) Assignee: Northeastern University, Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/197,896

(22) Filed: Nov. 23, 1998

Related U.S. Application Data

(62) Division of application No. 08/861,906, filed on May 22, 1997, now Pat. No. 5,840,388, which is a continuation of application No. 08/379,834, filed on Jan. 27, 1995, now abandoned.

(51) Int. Cl.[7] .......................... B32B 9/04; B32B 27/32; B29D 22/00
(52) U.S. Cl. ...................... 428/447; 428/521; 428/35.7; 428/36.91; 427/372.2; 427/387
(58) Field of Search .................... 428/35.7, 36.9, 428/36.91, 36.92, 446, 447, 442, 463, 521, 34.4, 34.7, 36.7; 204/451, 455, 601, 605; 427/372.2, 387

(56) References Cited

U.S. PATENT DOCUMENTS

| | | |
|---|---|---|
| 4,680,201 A | 7/1987 | Hjerten .................. 427/230 |
| 4,690,749 A | 9/1987 | Van Alstine et al. ........ 204/299 |
| 5,181,999 A | 1/1993 | Wiktorowicz ............ 204/180.1 |

(List continued on next page.)

FOREIGN PATENT DOCUMENTS

| | | |
|---|---|---|
| EP | 17048 A1 | 9/1994 |
| WO | 94105 61 | 5/1994 |
| WO | WO 96/23220 | 8/1996 |
| WO | WO 96/23221 | 8/1996 |

OTHER PUBLICATIONS

Huang, M., et al.., "Self–assembled Alkylsilane Monolayers for the Preparation of Stable and Efficient Coatings in Capillary Electrophoresis", *J. Microcolumn Separations*, vol. 6, No. 6 (1994), pp. 571–576. (No month).

Hjerten, S., "High–Performance Electrophoresis—Elimination of Electroendosmosis and Solute Adsorption", *Journal of Chromatography*, 347 (1985), pp. 192–198. (No month).

*Primary Examiner*—Harold Pyon
*Assistant Examiner*—Michael C. Miggins
(74) *Attorney, Agent, or Firm*—Weingarten, Schurgin, Gagnebin & Lebovici LLP

(57) ABSTRACT

Coatings suitable for surfaces such as are found in capillary electrophoresis columns and methods for their preparation are disclosed. A coated surface of the invention, preferably an interior surface of a microcapillary, generally includes a surface having an interconnected polymeric coating that includes a functional group attached to the surface and capable of copolymerizing with an organic compound in an organic solvent, and a polymer of the organic compound copolymerized with the functional group. The coating can be covalently or non-covalently attached to the surface and can further include an additional layer of coating material. Preferably, the organic compound is a vinyl ester, and most preferably, vinyl acetate, and the attached polymer forming the exposed surface of the coating is a polyvinyl alcohol, the hydroxyl groups of which can be further derivatized in any desired manner. The coating of the invention creates a new, stable surface, appropriate for CE columns or general surface modification. The coating is stable over a wide pH range and allows highly efficient grafting and/or adsorption of a variety of additional layers, if desired.

10 Claims, 12 Drawing Sheets

U.S. PATENT DOCUMENTS

| | | |
|---|---|---|
| 5,185,466 A | 2/1993 | Kozulic et al. ............... 564/208 |
| 5,192,406 A | 3/1993 | Woolley .................. 204/180.1 |
| 5,221,447 A * | 6/1993 | Hjerten .................... 204/180.1 |
| 5,228,960 A | 7/1993 | Liu et al. ................. 204/182.8 |
| 5,264,101 A | 11/1993 | Demorest et al. ........ 204/299 R |
| 5,296,114 A | 3/1994 | Manz ....................... 204/180.1 |
| 5,302,272 A | 4/1994 | Klein ..................... 204/299 R |
| 5,308,580 A | 5/1994 | Clark ........................... 422/58 |
| 5,310,462 A | 5/1994 | Chen .................... 204/180.1 |
| 5,312,535 A | 5/1994 | Waska et al. ........... 204/299 R |
| 5,314,593 A | 5/1994 | Swedberg ............... 204/180.1 |
| 5,318,680 A | 6/1994 | Fishman et al. ......... 204/180.1 |
| 5,318,686 A | 6/1994 | Dill et al. ................ 204/299 R |
| 5,322,608 A * | 6/1994 | Karger et al. ............... 204/299 |
| 5,324,401 A | 6/1994 | Yeung et al. ............. 204/180.1 |
| 5,324,412 A | 6/1994 | Kolner ................... 204/299 R |
| 5,324,413 A | 6/1994 | Gordon .................. 204/299 R |
| 5,326,445 A | 7/1994 | Lauer et al. ............. 204/180.1 |
| 5,328,578 A | 7/1994 | Gordon .................. 204/180.1 |
| 5,332,480 A | 7/1994 | Datta et al. .............. 204/180.1 |
| 5,348,658 A | 9/1994 | Fuchs et al. ................ 210/656 |
| RE34,757 E | 10/1994 | Smith et al. ............ 204/299 R |
| 5,364,520 A | 11/1994 | Okuyama et al. ....... 204/299 R |
| 5,369,717 A | 11/1994 | Attridge ...................... 385/12 |
| 5,605,613 A | 2/1997 | Shieh ........................ 204/451 |
| 5,840,388 A * | 11/1998 | Karger et al. ............. 428/36.91 |

* cited by examiner

COATED SURFACE COMPRISING A POLYVINYL ALCOHOL (PVA) BASED COVALENTLY BONDED STABLE HYDROPHILIC COATING

CROSS REFERENCE TO RELATED APPLICATIONS

This application is a divisional application of U.S. application Ser. No. 08/861,906, filed May 22, 1997, now U.S. Pat. No. 5,840,388, which is a file wrapper continuation application of U.S. application Ser. No. 08/379,834, filed Jan. 27, 1995, abandoned the whole of which are hereby incorporated by reference herein.

BACKGROUND OF THE INVENTION

Capillary electrophoretic separation techniques find wide application in the biologically related sciences. Molecular species such as peptides, proteins, oligonucleotides, and oligosaccharides are separated by causing them to migrate in a buffer solution under the influence of an electric field. The separation is normally carried out in thin-walled, narrow-bore capillary tubes to minimize the evolution of heat during electrophoretic separation, which would cause zone deformation.

Among the other mechanisms that can cause zone deformation are non-uniform electroendosmosis, excess electroosmotic flow, and solute adsorption to the inner surface of the capillary. However, these problems can be minimized or overcome by coating the inner wall of the electrophoresis tube with various polymeric substances.

In U.S. Pat. No. 4,680,201, Hjerten discloses a method for coating the inner wall of a narrow bore capillary with a monomolecular polymeric coating of polyacrylamide bonded to the capillary wall by means of a bifunctional reagent, e.g., γ-methacryloxypropyltrimethoxysilane. These capillaries can be used for free-zone electrophoresis in open tubes.

Novotny et al., U.S. Pat. No. 5,074,982, discloses that the inner wall of silica capillaries used in electrophoretic separations can be coated with bifunctional reagent using a Grignard reagent, for hydrolytic stability.

Thermal immobilization of adsorbed polyvinyl alcohol (PVA) as a coating on fused silica capillary surfaces is described in Gilges et al., Anal. Chem. 66:2038–2046 (1994). These coatings are stable for separations over a wide range of pH; however, at high buffer pH, the adsorption of PVA molecules and the suppression of analyte/wall interaction is weakened.

SUMMARY OF THE INVENTION

The present invention generally features coatings suitable for surfaces such as are found in capillary electrophoresis columns and methods for their preparation. A microcapillary column of the invention generally includes a microcapillary having an interior cavity and a wall with an inner surface, the inner surface of the wall having an interconnected polymeric coating that includes a functional group attached to the inner surface and capable of copolymerizing with an organic compound in an organic solvent and a polymer of the organic compound copolymerized with the functional group. The coating can be covalently or non-covalently attached to the column wall and can further include an additional layer of coating material. Preferably, the organic compound is a vinyl ester, and most preferably, vinyl acetate, and the attached polymer forming the exposed surface of the coating is a polyvinyl alcohol, the hydroxyl groups of which can be further derivatized in any desired manner. In a most preferred capillary column, the coating material includes a polyvinyl alcohol based polymer covalently attached to the column wall by Si—O—Si bonds.

The method of the invention generally includes providing a microcapillary, modifying the inner surface of the capillary wall to provide attached functional groups capable of copolymerizing with an organic compound in an organic solvent, introducing a solution of the organic compound in an organic solvent into the interior cavity of the microcapillary; and causing molecules of the organic compound to copolymerize with the attached functional groups to form an interconnected polymeric coating material attached to the inner surface of the microcapillary column. Preferably, the attached functional groups are covalently bonded vinyl groups, the organic compound is a vinyl ester, and the resulting interconnected polymeric coating material of polyvinyl ester is modified in a polymer homologous reaction to produce the desired polyvinyl alcohol coating.

In another aspect, the method of the invention features, in general, forming a column with a hydrophilic polymeric coating by directly converting an attached hydrophobic polymeric coating material to a hydrophilic coating material. The resulting hydrophobic polymeric coating can contain acidic, basic or neutral functionalities depending on the intended use of the column.

The terms "CE column" or "microcapillary column" are meant to include a vessel of any shape in which capillary electrophoresis can be carried out. For example, it is also known to use chips with open grooves microfabricated into the surface of the chip for capillary electrophoresis.

The coating of the invention creates a new, stable surface, appropriate for CE columns or general surface modification. The coating is stable over a wide pH range and allows highly efficient grafting and/or adsorption of a variety of additional layers, if desired. As used in capillary electrophoresis, the coating suppresses or controls electroosmotic flow and prevents adsorption of analytes to the surface of the column.

BRIEF DESCRIPTION OF THE DRAWINGS

Other features and advantages of the invention will be apparent from the following description of the preferred embodiments thereof, taken in conjunction with the accompanying drawings, in which.

DETAILED DESCRIPTION OF THE INVENTION

Figure 1:
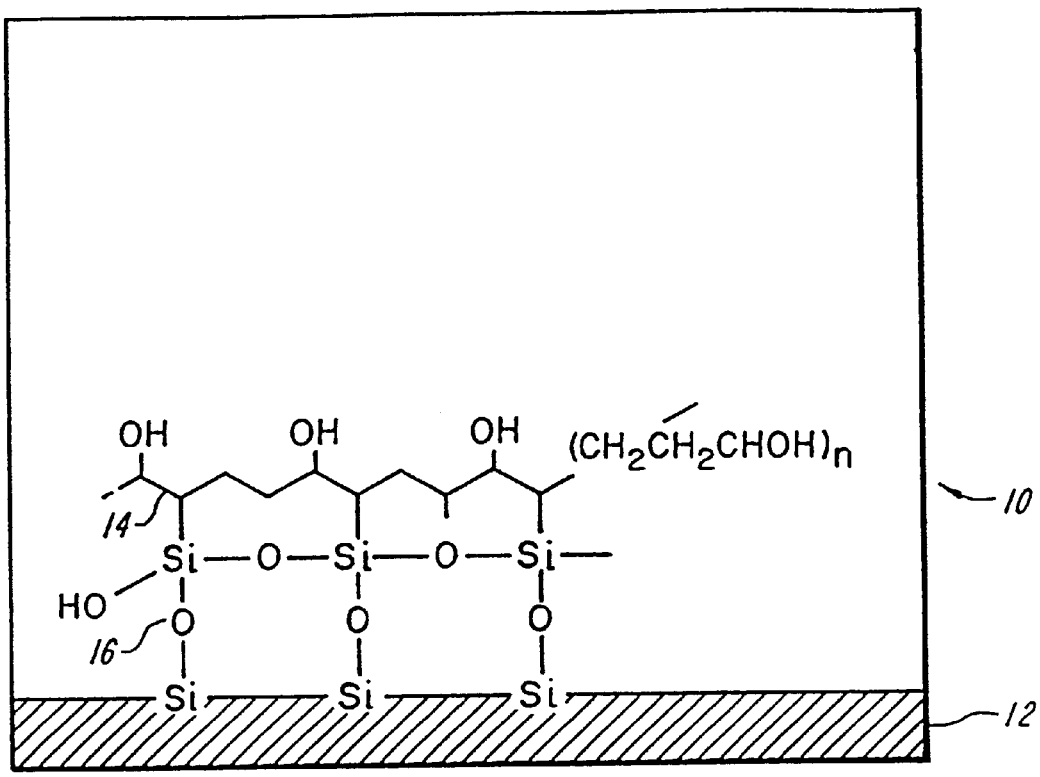
FIG. 1 shows a cross-sectional view of a coated microcapillary column of one embodiment of the invention in which an interconnected polyvinyl alcohol based polymeric coating is covalently attached to the inner wall of the column by Si—O—Si bonds.

The invention, as applied in capillary electrophoresis, provides a new method for obtaining highly stable hydrophilic coated microcapillary columns with superior performance for the separation of biopolymers. As shown in FIG. 1, a preferred microcapillary column of the invention includes a fused silica microcapillary 10 having an inner wall 12 and an interconnected polyvinyl alcohol based polymeric coating 14 covalently attached to inner wall 12 by Si—O—Si bonds 16.

A preferred method of the invention generally includes, as a first step, a silanization procedure which modifies the silica surface of the capillary with highly reactive vinyl silanol oligomers, leaving free vinyl groups as a reactive functionality. Next, a hydrophobic monomer (vinyl acetate) is copolymerized with the anchored vinyl groups in an organic solvent in the interior cavity of the surface modified, fused silica capillary. In the last step, the covalently bonded hydrophobic polymer (polyvinyl acetate) is converted into its hydrophilic counterpart (polyvinyl alcohol or PVA). (It is possible that some small amount of acetate groups may remain.) The preparation procedure for the polyvinyl alcohol-coated capillaries of the invention is simple, reliable and reproducible. No toxic chemicals are involved. The resulting hydrophilic coating is chemically and hydrolytically very stable and allows the efficient separation of biopolymers over a wide pH range.

The following procedure (which is described in more detail in the EXAMPLES) will result in a stable coating of polyvinyl alcohol, covalently attached to the surface of fused silica capillaries:

Surface Modification of the Fused Silica Capillary to Provide Stable, Covalently Bonded Groups for Copolymerization with Monomers of an Organic Compound.

Figure 2:
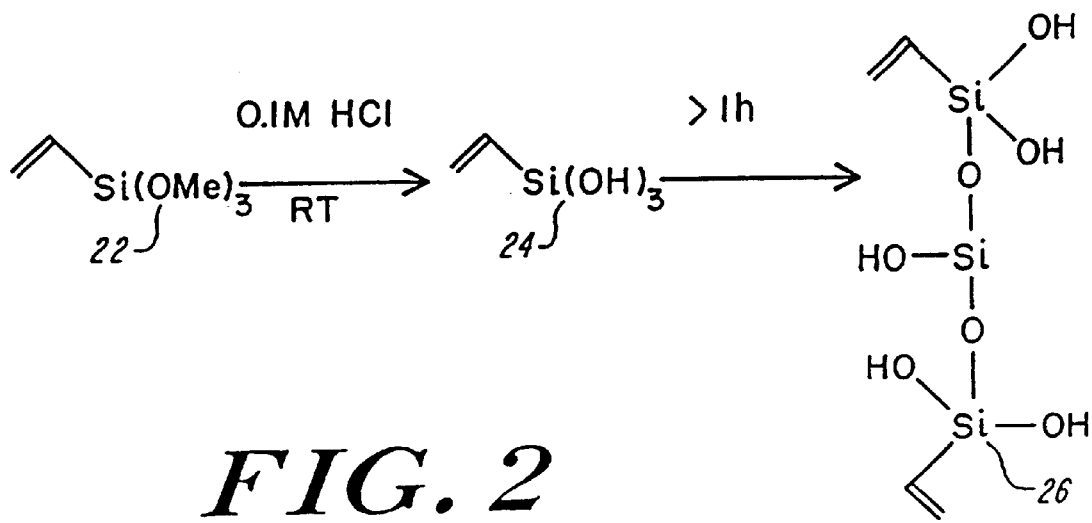
FIG. 2 shows the hydrolysis and condensation of vinyltrimethoxysilane to form a mixture of oligomeric vinylsilanol compounds as carried out in the surface modification step of one embodiment of the method of the invention.

To allow reproducible surface modification, the capillaries are first treated with acid to compensate for the different surface quality of the individual fused-silica capillaries (different manufacturers, different aging history from batch-to-batch). This procedure results in a more active capillary surface as well as a more uniform surface by increasing the number of exposed, reactive silanol groups. Actual modification of the capillary wall is achieved by reacting the surface silanols with a mixture of oligomeric vinylsilanol compounds. Referring to FIG. 2, these compounds are obtained in solution by reacting vinyltrimethoxysilane 22 with a limited amount of 0.1 M HCl. The acid cleaves off the protective methoxy group and converts the silane into a highly surface-reactive polysilanol species (vinylsilanetriol) 24. In addition, the vinylsilanetriol condenses to oligomers 26. The limited amount of water present prevents the compounds in the mixture from polymerizing and cross-linking, which would result in precipitation. It is to be noted that these silanization mixtures are stable for days.

Figure 3:
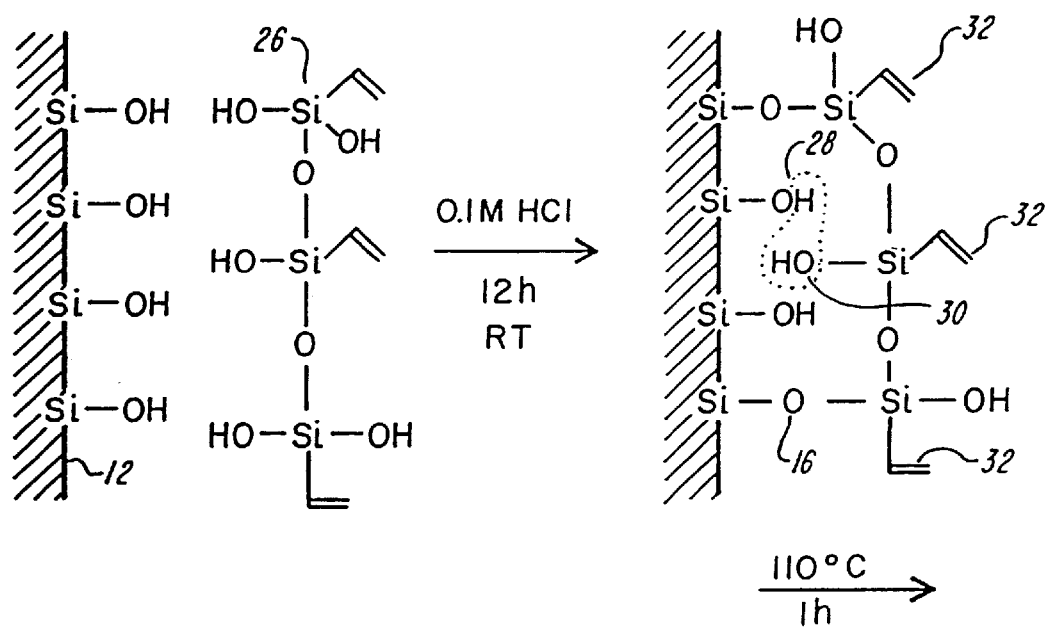
FIG. 3 shows attachment and curing of the oligomeric vinylsilanol compounds of FIG. 2 as carried out in the surface modification step of one embodiment of the method of the invention.

Referring to FIG. 3, the subsequent attachment of oligomers 26 to the capillary surface 12 (via the condensation of surface silanol groups 28 with oligomer silanol groups 30) results in a very stable Si—O—Si bond 16 and provides the surface with covalently bonded vinyl groups 32 which can copolymerize with vinyl acetate. The use of an olefinic, non-functional silane avoids any hydrolytically unstable functional groups in the attached molecule. In addition, due to the thermal stability of the vinylsilane group, a curing of the modified surface can be performed at high temperature (110° C. for 1 h), which increases stability of the coupling chemistry.

Polymerization of Vinyl Acetate Monomers within the Capillary Tube in an Organic Solvent.

Figure 4:
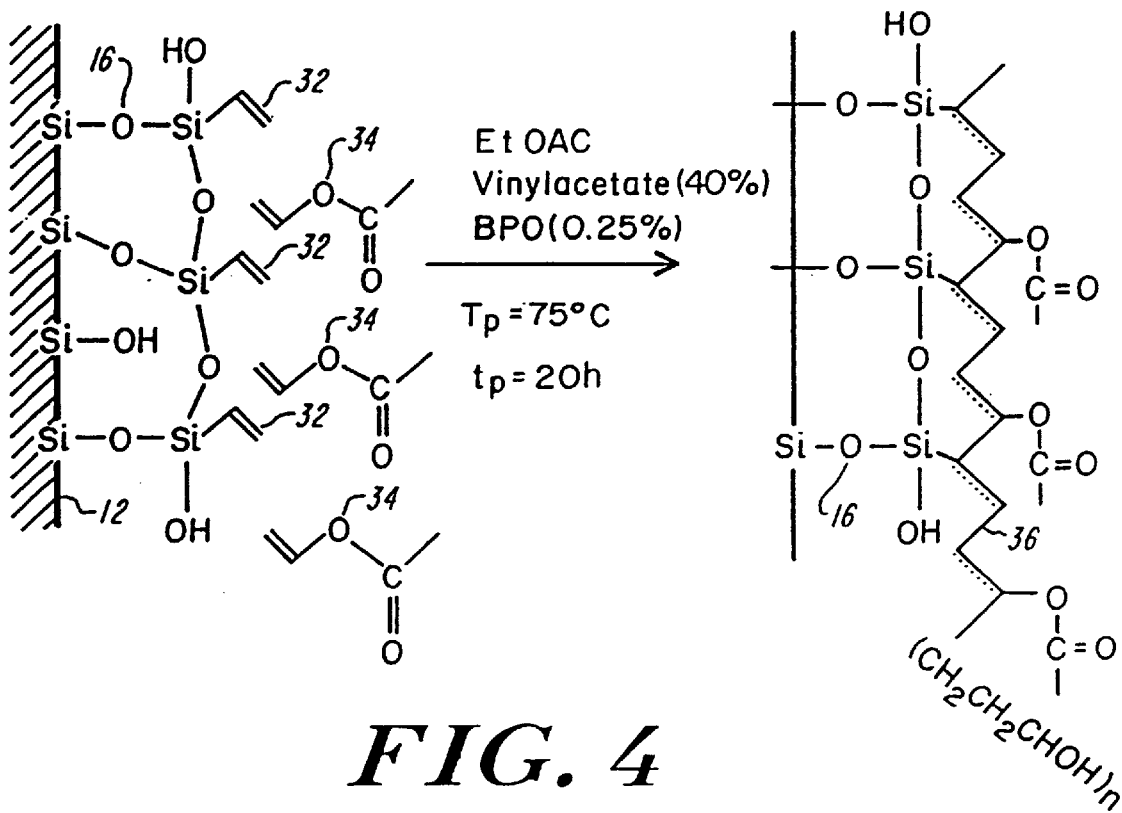
FIG. 4 shows copolymerization of the monomer vinylacetate with the vinyl groups of the attached oligomeric vinylsilanol compounds of FIG. 3 to form a covalently bonded hydrophobic polymer (polyvinyl acetate), according to one embodiment of the method of the invention.

As shown in FIG. 4, copolymerization of vinyl acetate monomers 34 with the vinyl groups 32 of the covalently bonded vinylsilanes on the capillary surface 12 results in covalent bonding of the resulting polyvinyl acetate 36 to the silica surface. (The dotted lines in the representation of polyvinyl acetate 36 in FIG. 4 indicate the earlier location of the double bonds in the vinyl acetate monomers. Those skilled in the art use the term polyvinyl acetate for the polymer of vinyl acetate monomers even though the resulting polymer no longer contains vinyl groups.)

Polymerization is initiated in an organic solvent, in the capillary tube, by the thermal decomposition of radical initiators such as α, α'-azodiisobutyronitrile or benzoyl peroxide, which start to decompose below the boiling point of the monomer. In appropriate circumstances, the polymerization solutions may be deposited as a thin film on the modified capillary wall. This polymerization procedure is not sensitive to trace amounts of oxygen, as is, e.g., the polymerization of acrylamide. Organic solvents such as ethyl acetate produce good polymerization yields. Since the viscosity of the resulting polymer solutions in organic solvents is very low, up to 40% monomer can be used for the polymerization, guaranteeing a high grafting density (copolymerization with the surface vinyls and thus covalent attachment of the polymer). Furthermore, excess polymer solution can easily be pushed out of the capillaries. (With acrylamide in aqueous solution, the density limits are about 7% monomer.)

Conversion of the Covalently Bonded Hydrophobic Polymer (Polyvinyl Acetate) into its Hydrophilic Counterpart (Polyvinyl Alcohol or PVA)

Figure 5:
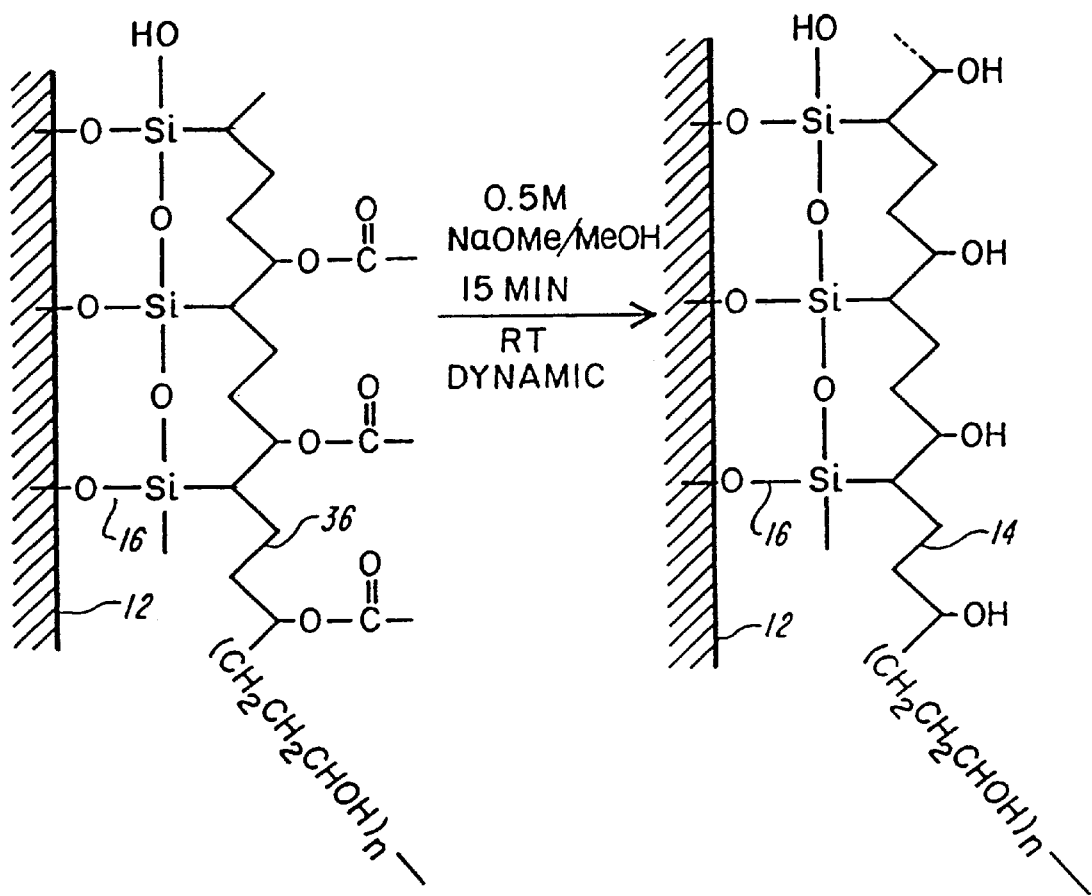
FIG. 5 shows conversion of the covalently bonded hydrophobic polymer (polyvinyl acetate) into its hydrophilic counterpart (polyvinyl alcohol or PVA)
Figure 6:
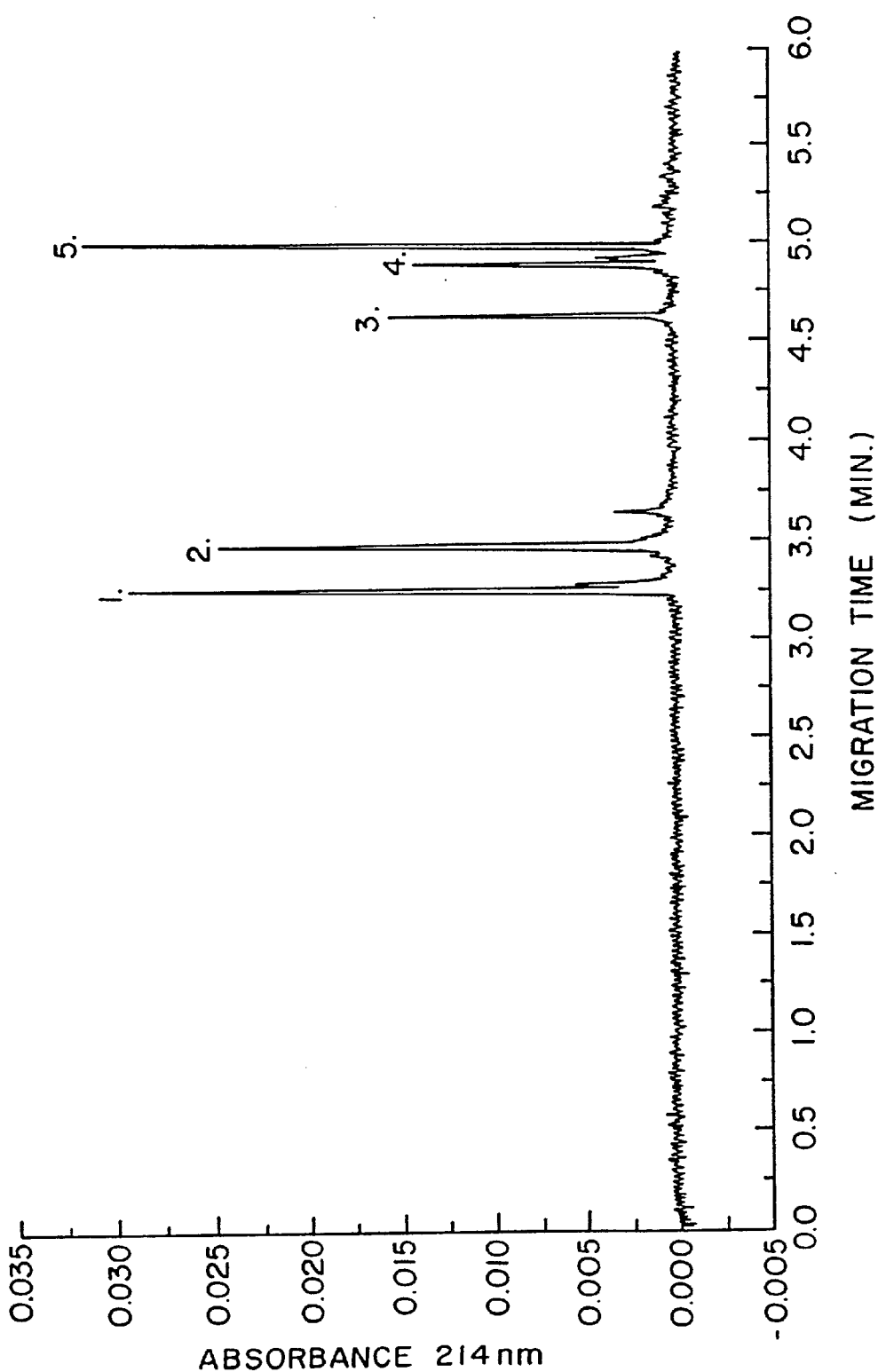
FIGS. 6–9 show open tube capillary zone electrophoresis of proteins at pH 4.4, 8.8, 6.2, and 10.0, respectively, using a microcapillary column of the invention.
Figure 7:
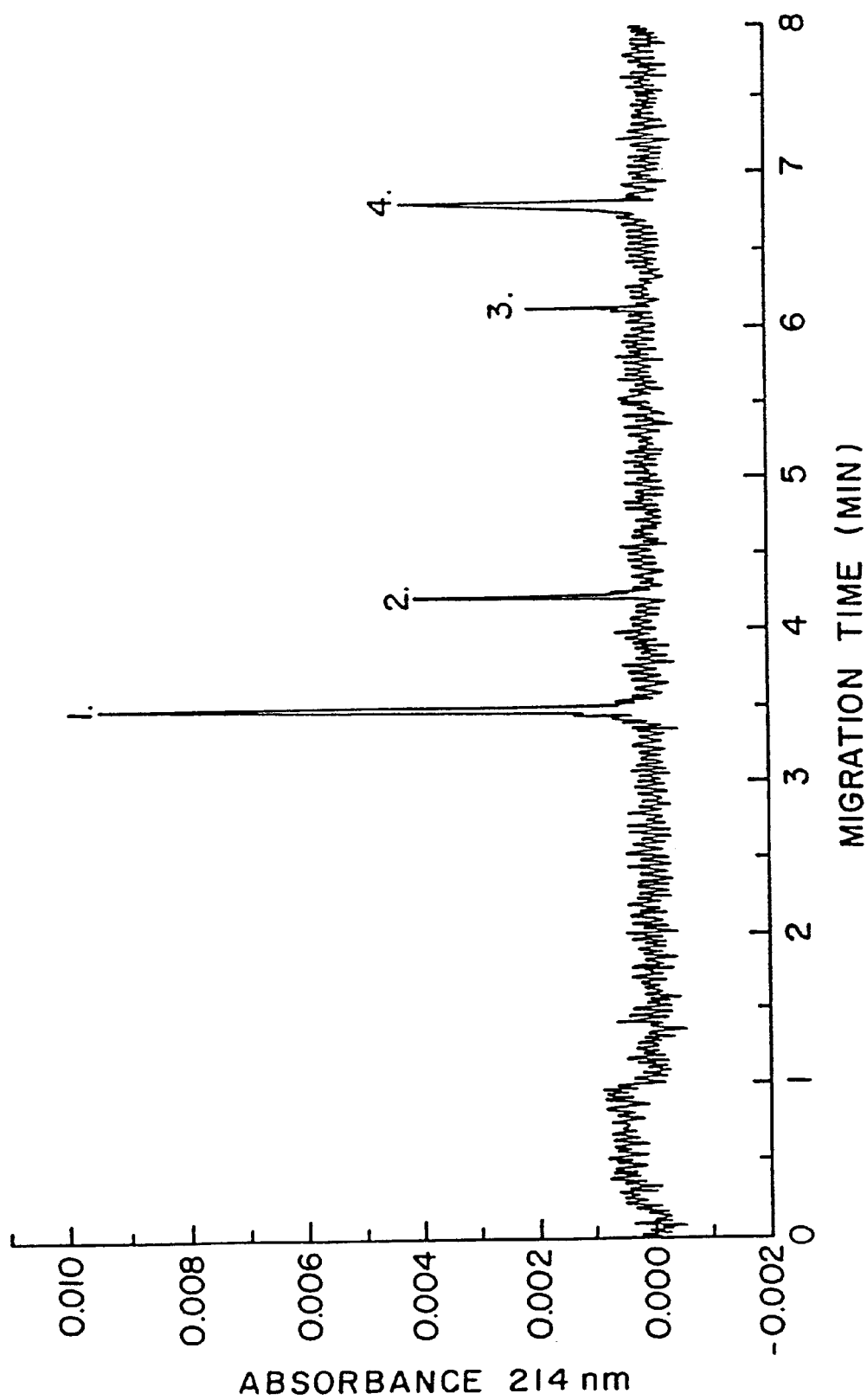
Figure 8:
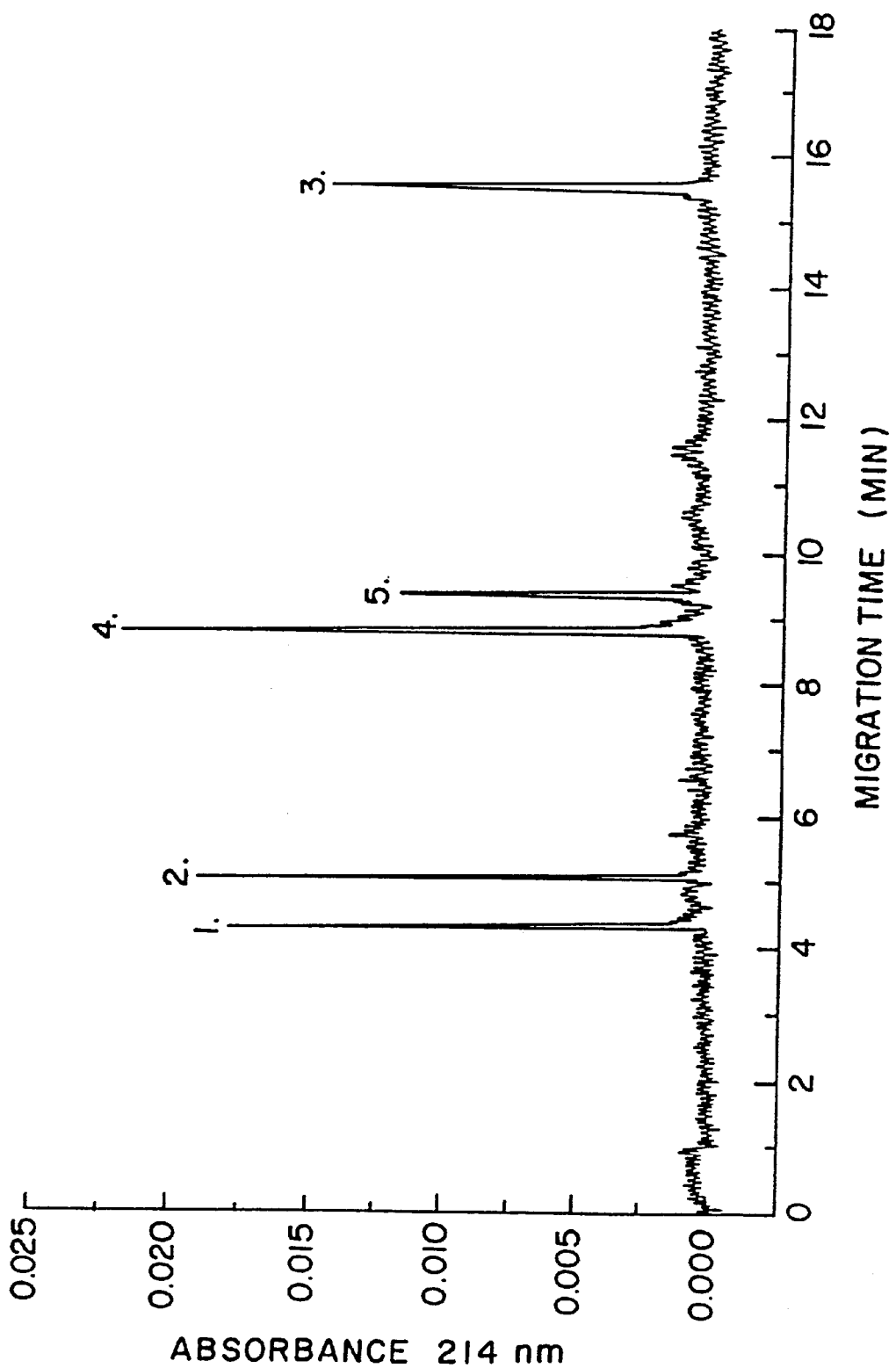
Figure 9:
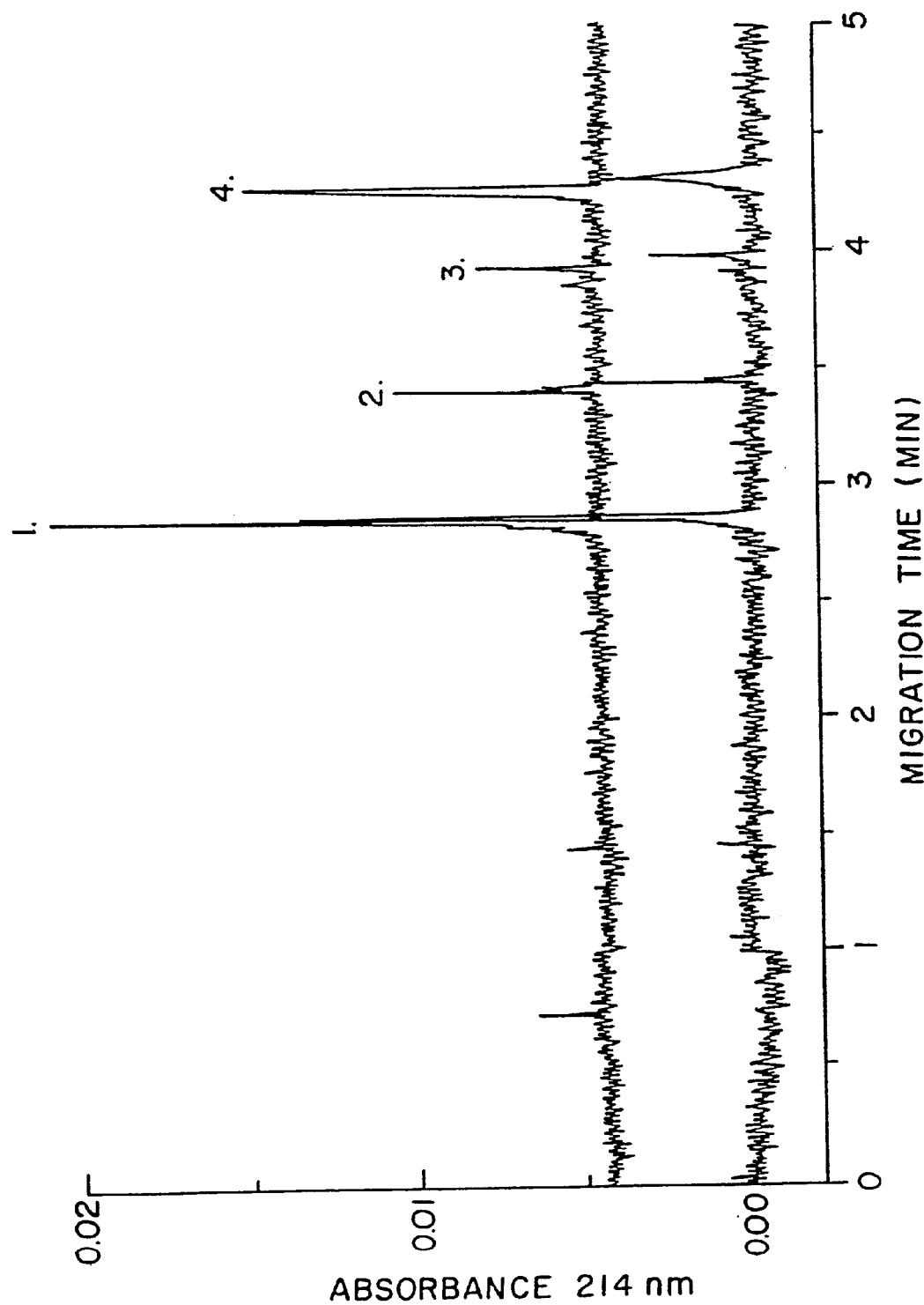
Figure 10:
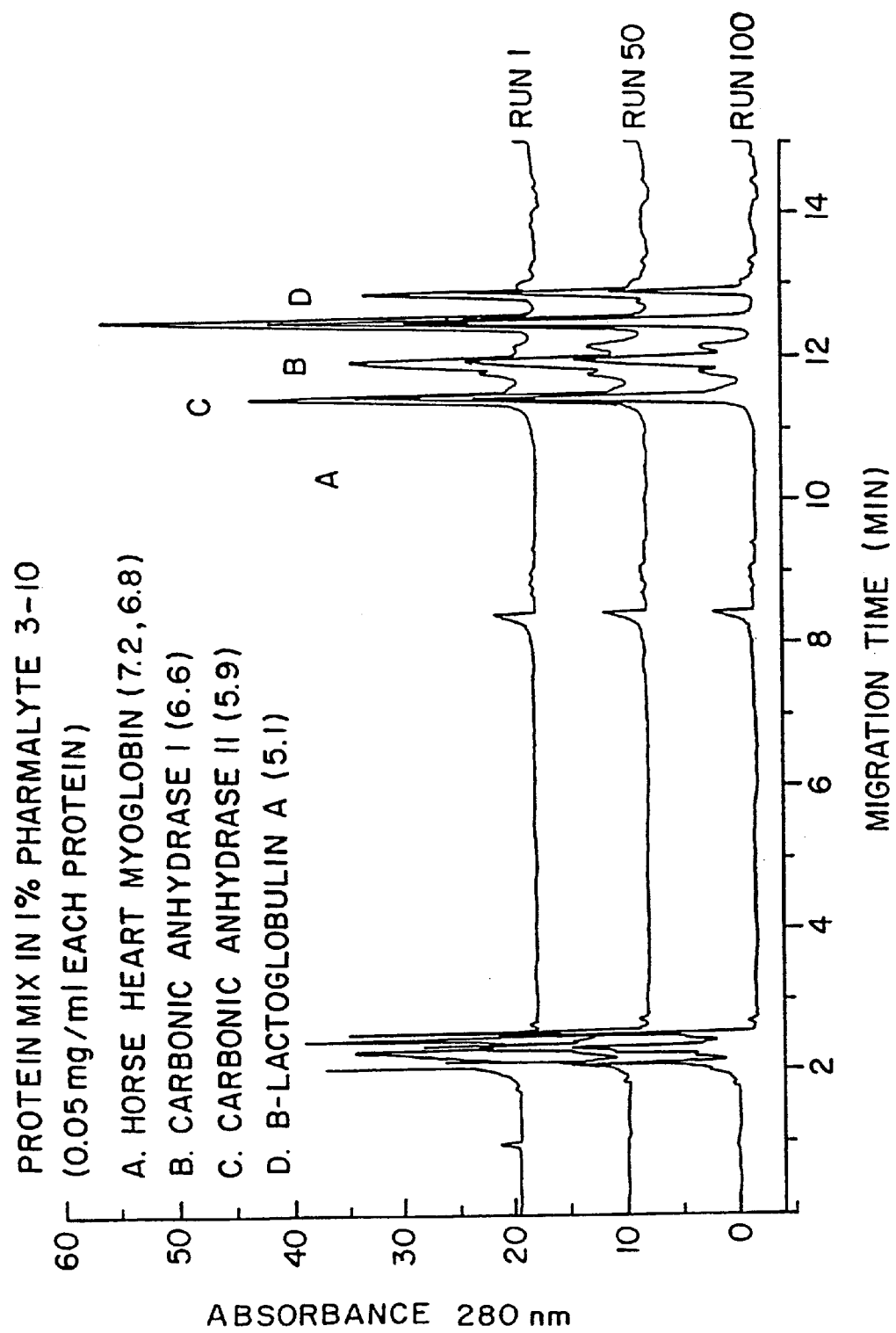
FIG. 10 shows isoelectric focussing of proteins using a microcapillary column of the invention.
Figure 11:
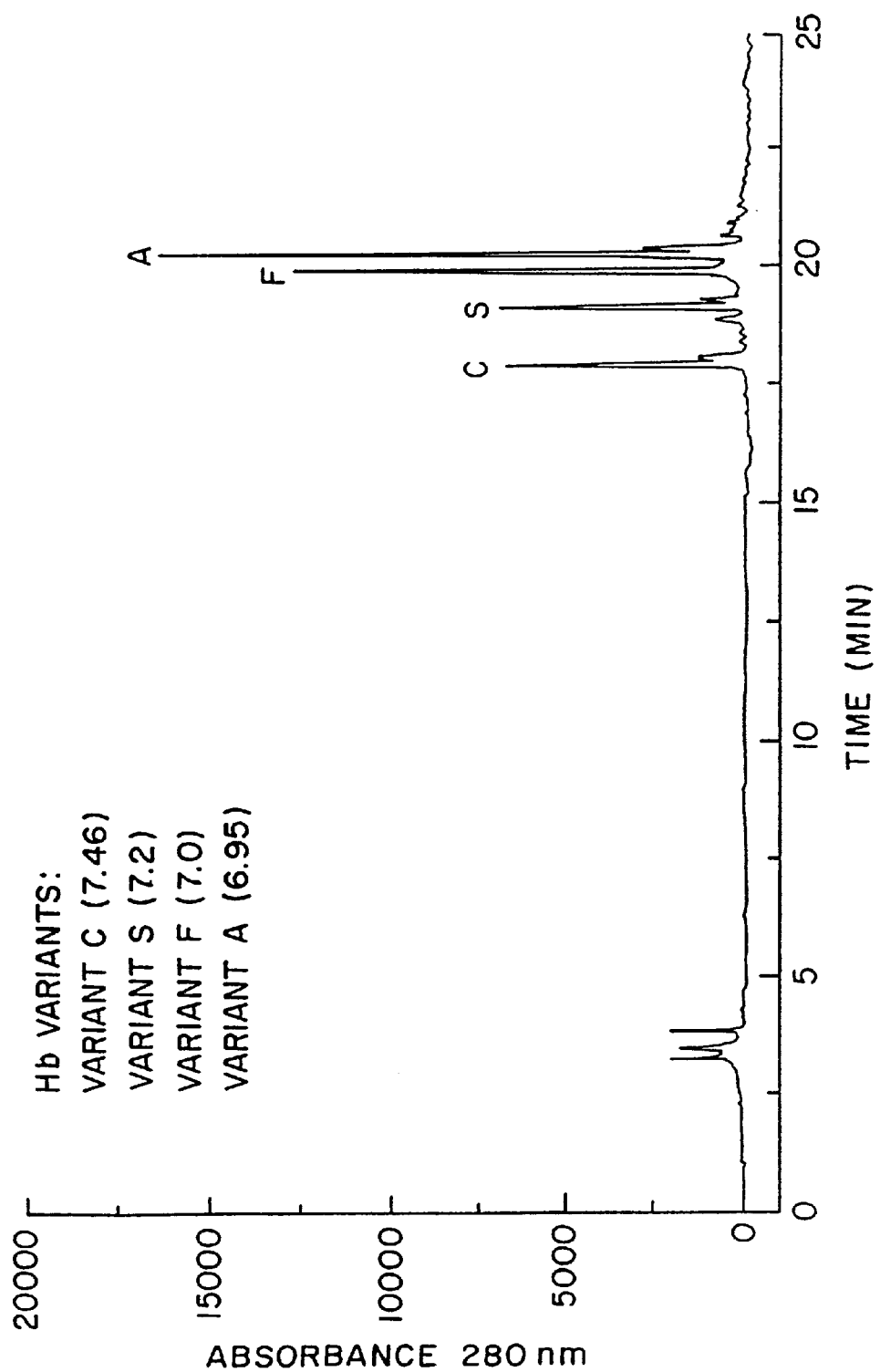
FIG. 11 shows isoelectric focussing of hemoglobin variants using a microcapillary column of the invention.
Figure 12:
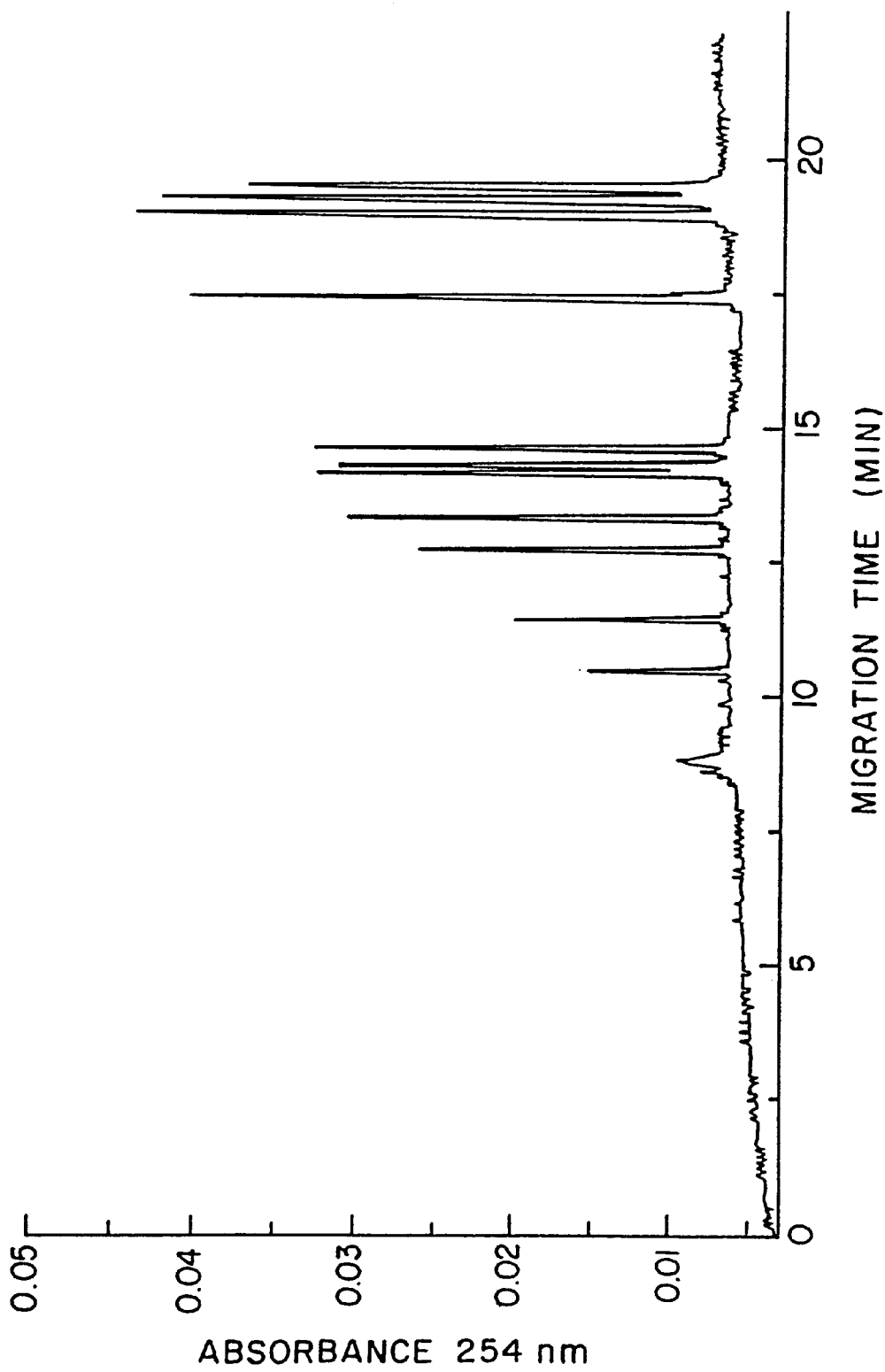
FIG. 12 shows open tube capillary zone electrophoresis of ΦX174 digested with Hae III, using a microcapillary column of the invention.
Figure 13:
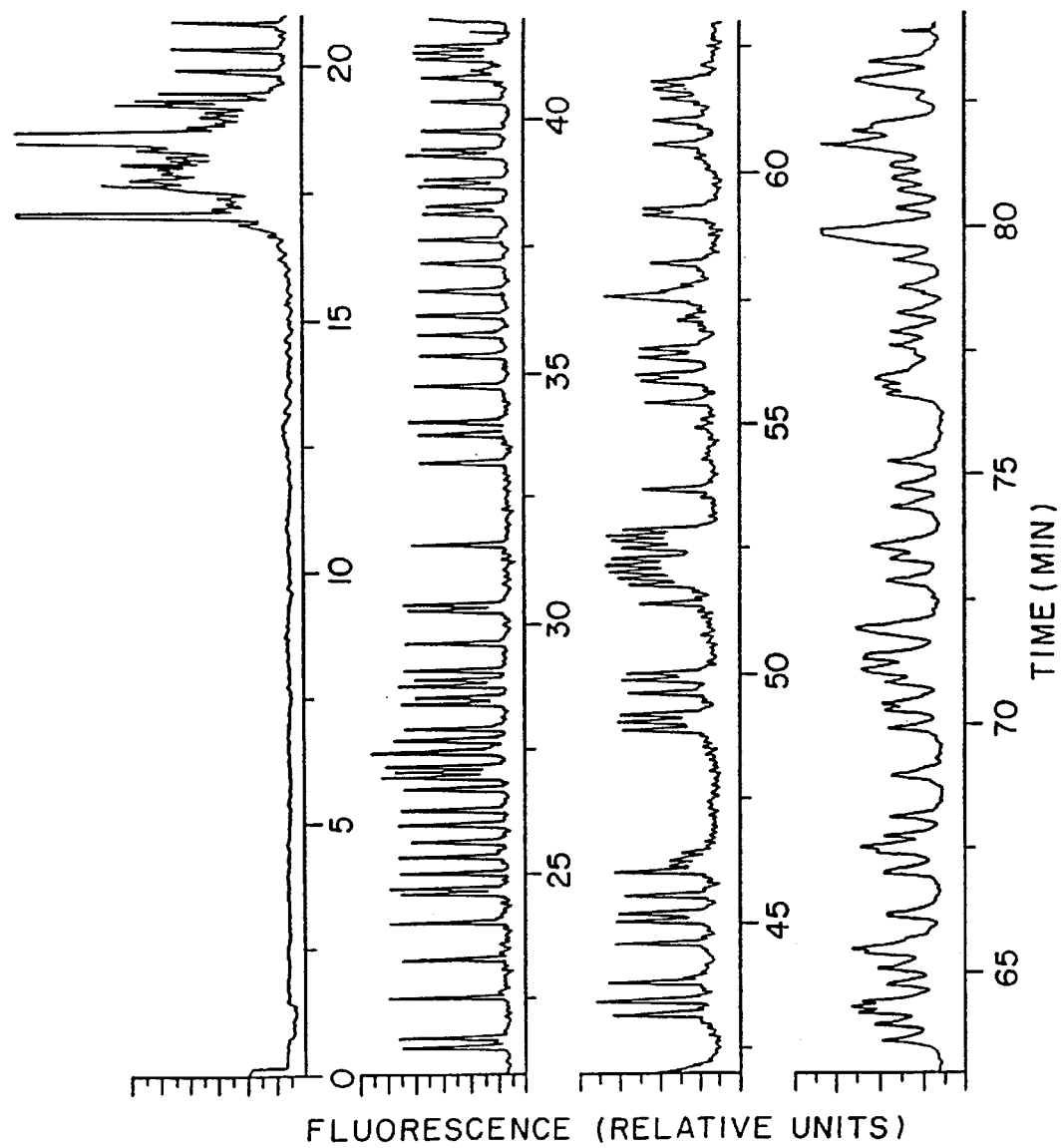
FIG. 13 shows polymer network separation of DNA sequencing reaction products using a microcapillary column of the invention.
Figure 14:
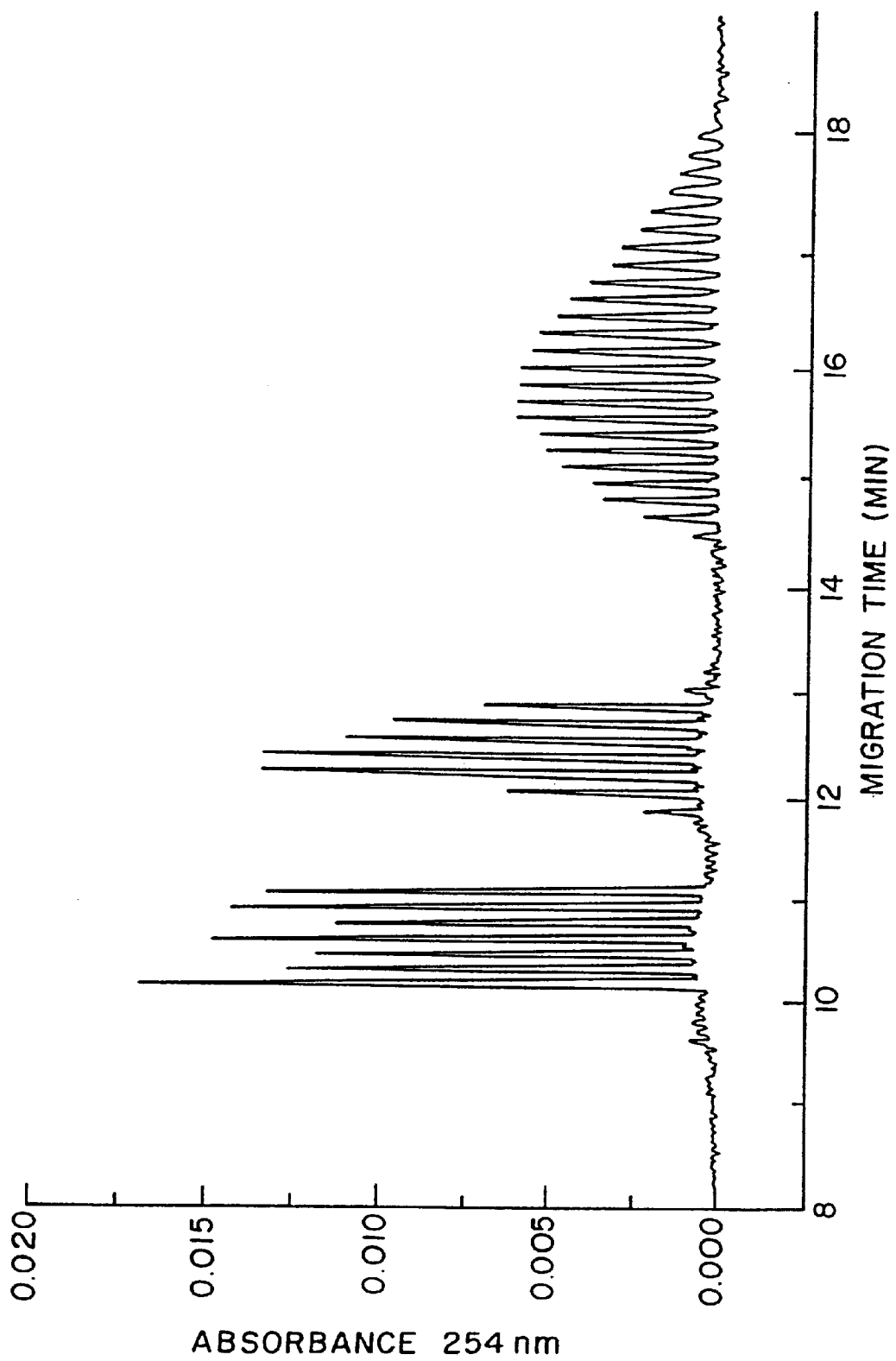
FIG. 14 shows polymer network separation of poly-dA oligonucleotides of various lengths using a microcapillary column of the invention.

After the hydrophobic polyvinyl acetate polymer is bound to the capillary surface, the coating has to be converted into its desired hydrophilic form, polyvinyl alcohol (PVA). Referring to FIG. 5, in a polymer homologous reaction, the covalently bonded polyvinyl acetate 36 can easily be deacetylated by flushing a solution of sodium methylate through the capillaries at room-temperature. Base-catalyzed deacetylation is very efficient even at ambient temperature; this step is conveniently carried out by flushing the sodium methylate solution through the capillary for a short period of time—about 15 minutes. As the hydrolysis of the ester group is performed under non-aqueous conditions, the silane chemistry is not affected by this strong base. Having anhydrous methanol as a solvent for hydrolysis precipitates the resulting polyvinyl alcohol 14, thus shielding the silane coupling chemistry underneath the polymer. The result of this procedure is a microcapillary with a hydrophilic, covalently attached coating of polyvinyl alcohol, which can be stored until use.

In comparison with, e.g., the polymerization of aqueous solutions of acrylamide within a capillary, the procedure described above offers several advantages. As polymerization is initiated by thermal decomposition of a radical initiator after the polymerizing solution has been injected into the capillary, the whole procedure is very convenient and controllable. In contrast, conventional polymerization of acrylamide in aqueous solution is initiated as soon as the ingredients (e.g., TEMED, APS, acrylamide monomers) are combined, and the solution must be handled quickly to prevent premature polymer formation. Polymerization in organic medium results in much lower viscosities of the polymer solution so that higher monomer concentrations can be used. This results in higher grafting density and thus better performance and stability. With 40% vinyl acetate, excess organic solvent can still easily be pushed out of the capillary after polymer formation, while in water, 7% acrylamide is about the limit. Liquid organic compounds that are polymerizable under the described conditions can, in fact, be used without any additional solvent. In this case, excess compound would be pushed out of the capillary after sufficient polymerization had occurred.

Polymerization in an organic solvent is less sensitive to oxygen than is polymerization in water, which allows the elimination of degassing steps and permits the use of chemicals as delivered from the manufacturer. This makes the overall procedure much more convenient and gives more reliable results. Finally, the chemicals (vinyl acetate, ethyl acetate and benzoyl peroxide) are much less toxic than those used in conventional, e.g., aqueous acrylamide, polymerization.

Use

The above method results in capillaries with excellent performance for the separation of proteins over a wide range of pH-values (see FIGS. 6–9). Even at almost neutral pH (pH=6.20, FIG. 8), excellent separation of proteins can be achieved under normal buffer conditions. A capillary run constantly at pH 10.0 at a voltage of 540 V/cm showed no loss in efficiency or shift in migration times after 7 days. In contrast, it is known that all acrylamide- or acrylate-based polymers become charged upon hydrolysis of functional groups at high pH. This condition results in peak deterioration and a shift in migration times for samples separated at high pH in polyacrylamide coated CE columns. Additionally, capillaries prepared according to the method of the invention have been used successfully for isoelectric focusing. Due to their chemical stability, excellent migration time reproducibility could be achieved.

Any of a variety of other vinyl esters could be used according to the method of the invention to make a polyvinyl alcohol coating, covalently bonded to the inner surface of a capillary column. In addition to the preferred ester, vinyl acetate, other appropriate vinyl esters include vinyl propionate, butyrate, benzoate, or laurate. Furthermore, the method of the invention is effective in forming a coating layer from any organic compound (monomer or oligomer) that is capable of copolymerizing in an organic solvent with functional groups attached to the capillary wall. Moderately hydrophobic monomers (e.g., vinylpyrrolidone, hydroxyalkyl(meth)acrylates, etc.) may be used to produce attached polymers that are sufficiently hydrophilic for use for CE separation of biopolymers in aqueous buffers without subsequent polymer homologous conversion.

The anchored functional groups can be attached covalently or non-covalently to the column wall. Functional groups that can copolymerize with vinyl esters preferrably include vinyl groups, but can also include any other functional group that can copolymerize in an organic solvent (such as allyl, acryl, methacryl or any other double-bond containing group). Other functional groups would be used for polymerizing with other polymerizable organic compounds.

The capillary is preferably made of fused silica and the anchored functional groups are preferably covalently attached to the inner surface of the column by the silane coupling chemistry described; however, other coupling methods will be obvious to those skilled in the art. The capillary may also be made of any organic polymer that already contains an appropriate functional group or that allows copolymerizable groups to be bonded to the surface.

Coating of other surfaces that are of importance in separation technologies (such as silica gel, polystyrene, etc.) could easily be carried out using the method of the invention. The preferred method described herein of applying a PVA coating is applicable to all silica surfaces (or polymer surfaces) modified with groups that can copolymerize with the monomer. This procedure would be of particular importance for HPLC, where surfaces with low protein adsorption are highly desirable, especially for size exclusion chromatography of proteins.

Coatings prepared by the method of the invention can easily be derivatized or modified to change surface chemistry or to attach an additional coating layer. For example, modifications to a covalently bonded PVA-coating (prepared as described) in a capillary or on the surface of silica gel can include crosslinking by bi-(or poly)functional reagents (such as diepoxides, diisocyanates, acid anydrides); chemical conversion of the polyhydroxy-coating into polyethers, polyesters, etc., by chemical reaction of the hydroxy-functionality with monomeric or polymeric reagents; linking of adjacent hydroxy-functionalities as in an epoxide or acetal; or reacting the functional surface with groups that would introduce charges and may result in an ion-exchange capacity of the surface. Thermal treatments may result in physical (orientation of the polymeric layer, hydrogen bonding, partial crystallization) or chemical (partial or complete condensation and thus crosslinking) modifications of the coating. Modification of the polymerization conditions or chemical conversion after polymerization to affect the distribution of 1,2- and 1,3-diols is also possible.

Use of borate containing buffers with a PVA coated column could result in complex formation with PVA hydroxyl groups. The resulting surface charge, at high pH, gives an EOF comparable to a bare fused silica capillary. Thus, PVA coated capillaries may be considered as capillaries with switchable (buffer dependent) EOF; with PVA coated HPLC-supports, borate buffers could be used to generate a dynamic cation exchanger.

The surface chemistry possible with PVA-coated silica surfaces allows for a broad range of chemical reactions as the surface can be considered in general as a polyhydroxy-compound (polyalcohol). This property is useful for forming affinity matrices for affinity CE or HPLC as antibodies, or other biospecific reagents, can easily be bonded to the coated surface via hydroxy-reactive groups. The PVA-coating beneath the attached antibodies would guarantee low adsorption and thus eliminate non-specific interaction.

The following examples are presented to illustrate the advantages of the present invention and to assist one of ordinary skill in making and using the same. These examples are not intended in any way otherwise to limit the scope of the disclosure.

EXAMPLE I

Preparation of a covalently bonded polyvinyl alcohol (PVA) coated capillary:

A) A length of about 60 cm of polyimide-coated fused silica capillary with an internal diameter of 75 μm is rinsed for 2 h with conc. HCl/H$_2$O (1:1) at a temperature of 110° C. to provide a surface with high silanol concentration for successful silane coupling chemistry. The capillary is then rinsed to neutral pH and dried in a gentle He stream.

B) The silanization solution is prepared by mixing 2 ml of vinyltrimethoxysilane and 0.4 ml of 0.1 M HCl. Upon stirring, the initial two phase mixture homogenizes due to hydrolysis of alkoxysilane groups and liberation of methanol, a very exothermic reaction. One hour is allowed for hydrolysis and condensation of the vinylsilanols. The solution of oligomeric vinylsilanols is pushed through the capillaries for 1 h and allowed to stand overnight. The next day the capillaries are rinsed with methanol. Curing is performed at 110° C. in a gentle He stream.

C) The polymerization solution is prepared by mixing 3 ml of ethyl acetate with 2 ml of vinyl acetate, resulting a concentration of vinyl acetate of 40% (V/V). The addition of 100 μl of a 5% solution of benzoyl peroxide in ethyl acetate yields an initiator concentration of 0.25%. The vinyl modified capillaries from B) are filled with the polymerization solution and the polymerization is performed at 75° C. for 20 h. The polymer solution is then pushed out, and the capillaries are rinsed with ethyl acetate and methanol to remove any non-bonded polyvinyl acetate.

D) To convert the covalently bonded polyvinyl acetate into polyvinyl alcohol, the coated capillaries from C) are rinsed for 15 min with a solution of 0.5 M sodium methylate in methanol. The capillaries are rinsed afterwards with methanol and then dried in a He stream.

EXAMPLE II (FIG. 6)

Sample: (1) lysozyme, (2) cytochrome C, (3) myoglobin, (4) trypsinogen, (5) α-chymotrypsinogen A (0.1 mg/ml each). Coating: PVA as described in Example I. Conditions: i.d.=75 μm; L=30/37 cm; buffer: 20 mM ε-aminocaproic acid, pH=4.40; injection: 4 sec at 5 kV; separation voltage: 20 kV.

EXAMPLE III (FIG. 7)

Sample: (1) glucose-6-phosphatedehydrogenase, (2) trypsin inhibitor, (3) L-asparaginase, (4) α-lactalbumin (0.1 mg/ml each). Coating: Example I. Conditions: i.d.=75 μm; L=30/37 cm; buffer: 20 mM TAPS/AMPD, pH=8.80; injection: 4 sec at 5 kV; separation voltage: 20 kV.

EXAMPLE IV (FIG. 8)

Sample: (1) lysozyme, (2) cytochrome C, (3) myoglobin, (4) trypsinogen, (5) α-chymotrypsinogen A (0.1 mg/ml each). Coating: Example I. Conditions: i.d.=75 μm; L=30/37 cm; buffer: 20 mM TRIS/cacodylic acid, pH=6.20; injection: 5 sec with pressure injection (PAC/E); separation voltage: 20 kV.

EXAMPLE V (FIG. 9)

Sample: (1) glucose-6-phosphatedehydrogenase, (2) trypsin inhibitor, (3) L-asparaginase, (4) α-lactalbumin (0.1 mg/ml each). Coating: Example I. Conditions: i.d.=75 μm; L=30/37 cm; buffer: 20 mM CAPS/NaOH, pH=10.0; injection: 4 sec at 5 kV; separation voltage: 20 kV.

EXAMPLE VI (FIG. 10)

Sample: (A) myoglobin (pl=7.2), (B) carbonic anhydrase 1 (pl=6.6), (C) carbonic anhydrase II (pl=5.9), (D) β-lactoglobulin A(pl=5.1) (0.1 mg/ml of each protein mixed 1:1 with 2% Pharmalyte (3–10)). Coating: Example I. Conditions: i.d.=50 μm; L=30/37 cm; focussing: at 25 kV; mobilization: low pressure (PAC/E) starting after 10 min (25 kV); anolyte: 20 mM H$_3$PO4; catholyte: 20 mM NaOH.

EXAMPLE VII (FIG. 11)

Sample: hemoglobin variants C (pl=7.45), S (pl=7.20), F (pl=7.00) and A (pl=6.95) (0.1 mg/ml each mixed with 1:1 with a 2% ampholine mixture (Pharmalyte, Servalyte and Ampholyte)). Coating: Example I. Conditions: i.d.=50 μm; L=30/40 cm; focussing: at 30 kV; mobilization: hydrodynamic (d H=5 cm) starting after 15 min (30 kV); anolyte: 0.5% acetic acid; catholyte: 0.25% ammonium hydroxide.

EXAMPLE VIII (FIG. 12)

Sample: ΦX174 digested with Hae III. Coating: Example I. Conditions: i.d.=100 μm; L=26.75/27.50 cm; sieving matrix: 1% methylcellulose (2% gives 4000 cps) in 40 mM TAPS/TRIS; injection: 5 sec at 5 kV; separation voltage: 5 kV.

EXAMPLE IX (FIG. 13)

Sample: FAM labeled primer sequencing reaction terminated with dideoxythymidinetriphosphate on M13mp18. Coating: Example I. Conditions: i.d.=100 μm; L=30/40 cm; sieving matrix: 4%T LPA in 40 mM TRIS/TAPS with 30% formamide and 3.5 M urea; separation voltage: 8 kV; injection: 5 sec at 8 kV.

EXAMPLE X (FIG. 14)

Sample: poly-dA oligonucleotides 12–18, 25–30 and 40–60. Coating: Example I. Conditions: i.d.=100 μm; L=20/27 cm; sieving matrix: 10% polyamide+45% DMSO+10% urea+35% TAPS/TRIS (50 mM); injection: 3 sec at 10 kV; separation voltage: 20 kV; temperature: 40° C.

EXAMPLE XI

Coating a stationary phase for use in HPLC with polyvinyl alcohol. A silica gel of 300 Å pore size and 5 μm particle diameter is modified with vinyl groups as described in Example I (B) for a fused silica surface or according to other procedures well known to those skilled in the art (E. P. Plueddemann, *Silane Coupling Agents*. Plenum, N.Y. (1982)) 5 g of the silica gel is suspended in a solution of 10 ml vinyl acetate and 30 ml ethyl acetate. After 25 mg of benzoyl peroxide is added, the suspension is heated up to 75° C. for 20 hours under stirring and reflux. The polymer solution is then removed with a G4 filter funnel, and the polyvinyl acetate coated silica gel is washed with ethyl acetate and methanol to remove any non-covalently adsorbed polymer. Homologous conversion of the bonded polyvinyl acetate into PVA is carried out by stirring the silica gel for 15 min in a 0.1 M solution of sodium methylate in methanol. Then the silica gel is washed with methanol and dried at a temperature of 60° C.

EXAMPLE XII

The PVA-coated silica gel of Example XI is packed into a HPLC column, and high performance (or high pressure) size exclusion chromatography (SEC) of proteins, nucleotides and synthetic polymers can be performed in organic or aqueous solvents.

EXAMPLE XIII

Preparation of affinity matrices from PVA-coated surfaces can be prepared according to procedures well known to those skilled in the art, as disclosed in, e.g., G. T. Hermanson, A. K. Mallia, P. K. Smith, *Immobilized Affinity Ligand Techniques*. Academic Press, San Diego (1992).

Other embodiments of the invention will be apparent to those skilled in the art from a consideration of this specification or practice of the invention as disclosed herein. It is intended that the specification and examples be considered as exemplary only, with the true scope and spirit of the invention being indicated by the following claims.

What is claimed is:

1. A coated surface comprising:
  (a) a surface and (b) a polymeric, surface-modifying coating essentially of polyvinyl alcohol or a derivative thereof, said coating being interconnected to said surface, said coating remaining stable and covalently attached to said surface at pH values comprising pH 4.4 to pH 10.0.

2. The coated surface of claim 1 wherein, in said coating, said polyvinyl alcohol based polymer is covalently attached to said surface by Si—O—Si bonds.

3. The coated surface of claim 1 wherein said surface is made of a material selected from the group consisting of fused silica, glass, polytetrafluoroethylene and polyether ether ketone.

4. The coated surface of claim 1 wherein said coating is further modified by
  a. derivatizing the reactive groups of said coating,
  b. attaching an additional coating layer to said coated surface, or
  c. thermally treating said coated surface.

5. The coated surface of claim 1 wherein said coating further comprises an additional layer of coating material.

6. The coated surface of claim 5 wherein said additional layer of coating material is covalently bonded to hydroxyl groups of said polyvinyl alcohol based polymer.

7. The coated surface of claim 1 wherein, in said coating, said polyvinyl alcohol based polymer comprises free hydroxyl groups.

8. The coated surface of claim 1 wherein, in said coating, said polyvinyl alcohol based polymer comprises derivatized hydroxyl groups.

9. The coated surface of claim 8 wherein said derivatized hydroxyl groups of said polyvinyl alcohol based polymer comprise hydroxyl groups on adjacent carbon atoms derivatized to form an epoxide or an acetal.

10. The coated surface of claim 1 wherein said coating is further modified by
  (a) cross-linking using bi-functional reagents,
  (b) reacting the hydroxy groups of said surface with monomeric or polymeric reagents,
  (c) linking adjacent hydroxy groups to form an epoxide or acetal,
  (d) reacting the hydroxy groups of said surface to convert said surface to an ion-exchange resin,
  (e) thermally treating said surface, or
  (f) reacting the hydroxy groups of said coating with borate buffer.

* * * * *

UNITED STATES PATENT AND TRADEMARK OFFICE
CERTIFICATE OF CORRECTION

PATENT NO. : 6,372,353 B2
DATED : April 16, 2002
INVENTOR(S) : Barry L. Karger et al.

It is certified that error appears in the above-identified patent and that said Letters Patent is hereby corrected as shown below:

Column 9,
Line 34, "coating essentially" should read -- coating consisting essentially --.

Signed and Sealed this

Thirtieth Day of September, 2003

JAMES E. ROGAN
*Director of the United States Patent and Trademark Office*